United States Patent [19]

Shmulewitz

[11] Patent Number: 5,791,349
[45] Date of Patent: Aug. 11, 1998

[54] APPARATUS AND METHOD OF BIOELECTRICAL IMPEDANCE ANALYSIS OF BLOOD FLOW

[75] Inventor: Ascher Shmulewitz, Mercer Island, Wash.

[73] Assignee: Urohealth, Inc., Newport Beach, Calif.

[21] Appl. No.: 634,758

[22] Filed: Apr. 17, 1996

[51] Int. Cl.$^6$ .................. A61B 5/05; A61B 5/02
[52] U.S. Cl. .................. 128/734; 128/693; 128/713
[58] Field of Search .................. 128/734, 741, 128/774, 795, 796, 639, 644, 693, 692, 691, 642, 713

[56] References Cited

U.S. PATENT DOCUMENTS

| | | |
|---|---|---|
| 3,340,867 | 9/1967 | Kubicek et al. |
| 3,651,318 | 3/1972 | Czekajewski . |
| 3,726,269 | 4/1973 | Webster, Jr. . |
| 3,915,155 | 10/1975 | Jacobson et al. . |
| 4,437,469 | 3/1984 | Djordjevich et al. . |
| 4,450,527 | 5/1984 | Sramek . |
| 4,671,295 | 6/1987 | Abrams et al. . |
| 4,722,347 | 2/1988 | Abrams et al. . |
| 4,836,214 | 6/1989 | Sramek . |
| 4,852,580 | 8/1989 | Wood . |
| 4,870,578 | 9/1989 | Vysin et al. . |
| 4,953,556 | 9/1990 | Evans . |
| 4,967,759 | 11/1990 | Teves . |
| 5,005,573 | 4/1991 | Buchanan . |
| 5,024,228 | 6/1991 | Goldstone et al. . |
| 5,080,107 | 1/1992 | Teves . |
| 5,125,406 | 6/1992 | Goldstone et al. . |
| 5,203,344 | 4/1993 | Scheltinga et al. . |
| 5,379,765 | 1/1995 | Kajiwara et al. .................. 128/642 |
| 5,453,086 | 9/1995 | Weber .................. 604/20 |
| 5,469,859 | 11/1995 | Tsoglin et al. . |
| 5,477,860 | 12/1995 | Essen-Moller .................. 128/716 |

OTHER PUBLICATIONS

"Bioelectrical Impedance Analysis in Body Composition Measurement", *National Institute of Health Technology Assessment Conference Statement*, Dec. 12–14, 1994, pp. 3–35.

"Continuous Cardiac Output Monitoring by Electrical Bioimpedance", *American College of Cardiology*, Jun. 1988, pp. 1–7.

B. Bhattacharya et al., "Potential Distribution in the Thorax in Relation to Electrical Field Plethysmography", *Medical & Biological Engineering & Computing*, May 1988, pp. 303–309.

F. H. Bonjer, M.D., et al., "The Origin of the Variation of Body Impedance Occurring During the Cardiac Cycle", *Circulation*, vol. VI, Sep. 1952, pp. 415–420.

David E. Clarke, M.D., et al., "Thoracic Electrical Bioimpedance Measurement of Cardiac Output—Not Ready for Prime Time", *Critical Care Medicine*, vol. 21, No. 8, Aug. 1993, pp. 1111–1112.

H. Fuller, et al., "The Current Status and Future Directions of Impedance Cardiography in ICU", *Annals of Biomedical Engineering*, vol. 17, 1989, pp. 483–493.

(List continued on next page.)

*Primary Examiner*—V. Millin
*Assistant Examiner*—Robert N. Wieland
*Attorney, Agent, or Firm*—Fish & Neave; Nicola A. Pisano

[57] ABSTRACT

Apparatus and methods are provided for monitoring cardiac output using bioelectrical impedance techniques in which one or more interior electrodes are placed in the trachea in the vicinity of the ascending aorta, and one or more exterior electrodes are disposed near the suprasternal notch, so that the resulting bioelectrical impedance measurements reflect voltage changes induced primarily by blood flow dynamics, rather than respiratory or non-cardiac related physiological effects. Apparatus and methods are also provided so that the measured cardiac output may be used to control administration of intravenous fluids to a patient or to optimize heart rate for those patients having pacemakers.

23 Claims, 5 Drawing Sheets

OTHER PUBLICATIONS

David B. Geselowitz, "An Application of Electrocardiographic Lead Theory to Impedance Plethysomography", *III Transactions on Bio–Medical Engineering*, vol. BME–18, No. 1, Jan. 1971, pp. 38–41.

Joseph C. Greenfield, Jr., M.D., et al., "Relation Between Pressure and Diameter in the Ascending Aorta of Man", *Circulation Research*, vol. X, May 1962, pp. 778–781.

Harry Handelsman, D.O., "Public Health Service Assessment Cardiac Output by Electrical Bioimpedance", *Health Technology Assessment Reports: Cardiac Output by Electrical Bioimpedance*, No. 3, 1989, pp. 1–5.

Deok W. Kim et al, "Origins of the Impedance Change in Impedance Cardiography by a Three–Dimensional Finite Element Model", *IEEE*, 1988, pp. 993–1000.

W.G. Kubicek, "On the source of Peak First Time Derivative (dZ/dt) During Impedance Cardiography", *Annals of Biomedical Engineering*, vol. 17, 1989, pp.459–462.

John Lehr, "A Vector Derivation Useful in Impedance Plethysmographic Field Calculations", *IEEE Transactions on Biomedical Engineering*, Mar. 1972, pp. 156–157.

Henry C. Lukaski, PhD, et al., "Estimation of body Fluid Volumes Using Tetrapolar Bioelectrical Impedance Measurements", *Aviation, Space and Environmental Medicine*, Dec. 1988, pp. 1163–1169.

Daniel S. Miles, PhD et al., "Impedance Cardiography: Noninvasive Assessment of Human central Hemodynamics at Rest and During Exercise", *Exercise and Sport Sciences Reviews*, vol. 17, 1989, pp. 231–263.

Christos G. Pappas, M.D. et al., "Impedance Cardiography in the Measurement of Cardiac Output: Studies in Rabbits", *Journal of Surgical Research* 59, 1995, pp. 504–510.

R.P. Patterson, "Fundamentals of Impedance Cardiography", *IEEE Engineering in Medicine and Biology Magazine*, Mar. 1989, pp. 35–38.

Bill C. Penney, PhD, et al., "An Overview of the Theory and Some Applications of Impedance Plethysmography", *IEEE Frontiers of Engineering in Health Care*, 1981, pp. 169–173.

Andrew Sherwood et al., "Committee Report; Methodological guidelines for Impedance Cardiography", *Psychophysiology*, Feb. 1989, pp. 1–38.

William C. Shoemaker, MD, FCCM, et al., "Multicenter Trial of a New Thoracic Electrical Bioimpedance Device for Cardiac Output Estimation", *Critical Care Medicine*, vol. 22, No. 12, 1994, pp. 1907–1912.

Joseph M. VanDeWater, M.D. et al., "Development and evaluation of a New Impedance Cardiograph", *Journal of Clinical Engineering*, May/Jun. 1995, pp. 218–223.

Li Wang, "Contributions of Heart Movement and Blood Volume Change to Impedance Cardiography Calculated by Human Thorax Models", *IEEE*, 1993, pp. 808–809.

Li Wang, "Multiple Sources of the Impedance Cardiograpm Based on 3–D Finite Difference Human Thorax Models", *IEEE*, 1995, pp. 141–148.

Klaas R. Visser, Electrical Properties of Flowing Blood and Impedance Cardiography, *Annals of Biomedical Engineering*, vol. 17, 1989, pp. 463–473.

Xiang Wang, PhD et al., "Time–Frequency Distribution Technique in Biological Signal Processing", *Biomedical Instrumentation & Technology*, May–Jun. 1995, pp. 203–212.

APPARATUS AND METHOD OF BIOELECTRICAL IMPEDANCE ANALYSIS OF BLOOD FLOW

FIELD OF THE INVENTION

The present invention relates generally to apparatus and methods for non-invasively measuring cardiac output and more particularly to apparatus and methods for measuring cardiac output using bioelectrical impedance analysis techniques.

BACKGROUND OF THE INVENTION

Knowledge of cardiac output is crucial in the care of the critically ill patient, as well as patients with chronic heart disease requiring monitoring of medication. For many years the standard of cardiac output measurement has been pulmonary artery catherization. Previously known catherization techniques, as described, for example, in U.S. Pat. Nos. 3,915,155, 3,726,269 and 3,651,318, involve periodic injection into the patient's bloodstream of a bolus of heated saline, during which thermodilution measurements are performed to determine cardiac output. Such techniques cannot generally be used for continuous monitoring. Moreover, such catherization techniques pose significant risk to the patient, including malignant arrhythmias, pulmonary artery rupture, and in rare cases, death.

Consequently, for many years work has been underway to develop less invasive apparatus and methods for monitoring cardiac output. For example, as an alternative to catherization methods, Doppler ultrasound techniques have been adapted to measure the velocity of blood flow. Provided that the diameter of a vessel, its flow profile, and the angle of the ultrasound beam relative to the vessel can be determined, Doppler ultrasound measurements of the ascending aorta, either externally from the suprasternal notch, or internally from within the trachea, can be used as a measure of cardiac output.

U.S. Pat. No. 4,671,295 describes an example of such methods and apparatus, wherein an ultrasound transducer is mounted on the tip of an endotracheal tube so that Doppler measurements of blood flow from a point (pulse wave mode) or path (continuous wave mode) along the ultrasound beam can be measured. The method described in the patent requires multiple measurements within the blood vessel, a priori knowledge of the blood flow pattern and cross-sectional area of the vessel, and the relative angulation of the blood vessel. In addition, the measurement is highly dependent upon the exact placement of the transducer. These drawbacks have resulted in the slow adoption of Doppler ultrasound cardiac output techniques.

A yet further technique which the prior art has sought to apply to the measurement of cardiac output is bioelectrical impedance analysis (BIA). BIA has recently gained wide use as a method of measuring body composition and physiological metrics. BIA involves measurement of the electrical impedance (electrical resistance plus reactance) of body tissues as a function of the voltage drop experienced by a low level alternating current electric current that is passed through the body tissues between multiple electrodes.

Generally, BIA apparatus employ two excitation electrodes between which a low level current is conducted, and two sense electrodes disposed at intermediate locations for sensing tissue impedance. Current flows predominantly through materials with high conductivities, such as blood. Less current flows through muscle, which has an intermediate conductivity, while the conductivity of fat, air and bone is much lower than that of either blood or muscle. Since the resistance to flow is a function of the conductivity and cross-sectional area of the conducting volume, volumes having a larger cross-sectional area provide lower resistance.

It is also known that the impedance of the conducting volume and the measured medium metrics (i.e., static parameters such as fat or water content, and dynamic metrics, such as blood flow) are dependent upon the placement of the electrodes and the conducting path between the electrodes. Thus, the greater the distance between the electrodes, the more likely that extraneous variables will effect the measurement.

BIA methods generally correlate the measured voltage drop between the electrodes using relatively simple algorithms based on simplified models of body structure, for example, by assuming that the body is composed of simple cylindrical resistive volumes. Temporal cyclical variations in the body impedance are then assumed to be a result of physiological events such as blood flow and breathing.

Measurements of the electrical impedance, and particularly, how the electrical impedance varies with time, can therefore provide a non-invasive indicator of those events. Various algorithms have been developed to isolate the specific physiological parameters, such as cardiac output from the measured bioelectrical impedance, as described, for example, in W. G. Kubicek, et al., "Development And Evaluation Of An Impedance Cardiac Output System," *Aerospace Medicine*, Vol. 37, pp. 1208–1212 (1966), which is incorporated herein by reference.

Despite the application of BIA methods for measuring cardiac output, no simple continuous BIA-based cardiac output measurement device has gained widespread acceptance. Many existing BIA devices use external or internal electrodes to measure bioelectrical impedance for large volumes, for example, the whole body or thoracic segments. Because the sense current diffuses throughout the entire volume, making use of any and all conductive paths, differences between individual patients, and even for the same patient over time, may inhibit standardizing the BIA metrics.

Moreover, it is known that while BIA measurements of cardiac output provide good correlation for normal patients and those hemodynamically stable patients, there is poorer correlation for critically ill patients and patients in heart failure, as described, for example, in R. J. Detemeter et al., "The Use Of Noninvasive Bioelectric Impedance To Determine Cardiac Output: Factors Affecting Its Accuracy," *Am. J. Noninvasive Cardiol.*, Vol. 2, pp. 112–118 (1988), which is incorporated herein by reference.

An example of an attempt to overcome the variabilities encountered when taking bioelectrical impedance measurements across large volumes is described, for example, in U.S. Pat. No. 4,870,578. That patent describes BIA apparatus for monitoring cardiac output by using external electrodes that measure the electrical resistance of a segment of the thorax and includes circuitry to account for large voltage changes due to respiratory-induced voltage changes. As acknowledged in that patent, the respiratory-induced voltage changes are typically much greater than the cardiac-induced voltage changes.

Other devices that attempt to account for the affect of non-cardiac physiological events on bioelectrical impedance include arranging multiple electrodes on catheters for insertion into the esophagus to measure thoracic bioelectric impedance, as described, for example, in U.S. Pat. Nos. 4,852,580 and 4,836,214. Both patents describe multielectrode arrays inserted into the esophagus to provide an impedance measurement reflecting blood flow in the descending aorta. Such devices are not believed to provide true isolation of cardiac-induced voltage changes from those induced by other physiological events. In addition, these systems may be unable to provide positive contact of the multiple electrodes with the wall of the esophagus.

In view of the foregoing, it would be desirable to provide apparatus and methods for accurately, non-invasively and continuously measuring cardiac output using BIA techniques.

It further would be desirable to provide apparatus and methods for measuring cardiac output in critically ill patients using BIA techniques that overcome the inaccuracies arising from measuring voltage changes across whole body or large volume thoracic segments.

It also would be desirable to provide inexpensive apparatus and methods for measuring cardiac output using BIA techniques that overcome the drawbacks of previously known BIA cardiac output measurement devices and methods.

It would further be desirable to provide methods and apparatus for continuously monitoring cardiac output so as to permit the measured cardiac output to be employed as a metric for controlling and maintaining other aspects of a patient's health.

SUMMARY OF THE INVENTION

In view of the foregoing, it is an object of this invention to provide apparatus and methods for accurately, non-invasively and continuously measuring cardiac output using BIA techniques.

It is another object of this invention to provide apparatus and methods for measuring cardiac output in critically ill patients using BIA techniques that overcome the inaccuracies arising from measuring voltage changes across the whole body or large-volume thoracic segments.

It is yet another object of the present invention to provide inexpensive apparatus and methods for measuring cardiac output using BIA techniques that overcome the drawbacks of previously known BIA cardiac output measurement devices and methods.

It is still another object of this invention to provide methods and apparatus for continuously monitoring cardiac output that permit the measured cardiac output to be employed as a metric for controlling and maintaining other aspects of a patient's health.

These and other objects of the invention are accomplished in accordance with the principles of the invention by providing BIA cardiac output monitoring apparatus that measure only those volumes necessary to acquire cardiac output information. Apparatus in accordance with the present invention includes one or more interior electrodes placed in the trachea in the vicinity of the ascending aorta, and one or more exterior electrodes disposed in the vicinity of the suprasternal notch. Sense current conducted between the interior and exterior electrodes flows primarily through high-conductivity blood, so that voltage changes are induced primarily by blood flow dynamics, rather than respiratory or non-cardiac related physiological effects.

Methods in accordance with the present invention overcome the inaccuracies of the gross physiologic models employed in previously known BIA cardiac methods, by avoiding the simplified algorithms for the ventricular stroke volume based on whole thorax BIA measurements. In particular, the methods of the present invention avoid the inaccuracies in whole body or thoracic BIA measurements associated with ignoring the multiple, branched and complex paths of blood flow.

In accordance with the present invention, the capability to obtain BIA measurements in the vicinity of the ascending aorta, which has no branches, and which therefore directly reflects the flow of blood through the ascending aorta, provides a simple and highly accurate metric for computing ventricular stroke volume.

In yet further aspects of the present invention, the apparatus for monitoring a patient's cardiac output may be used to control administration of intravenous fluids to a patient or to optimize heart rate for those patients having pacemakers.

Further features of the invention, its nature and various advantages will be more apparent from the accompanying drawings and the following detailed description of the preferred embodiments.

DETAILED DESCRIPTION OF THE PREFERRED EMBODIMENTS

The present invention relates generally to the use of BIA techniques for measuring cardiac output in critically ill and heart-diseased patients. The apparatus and methods of the present invention overcome drawbacks observed in previously known attempts to use whole body or large volume thoracic BIA measurements to measure cardiac output, by providing apparatus and methods that are not based upon the gross modelling of physiological events implicit in such previously known BIA measurement techniques.

In the exemplary embodiments of the apparatus and methods of the present invention, one or more interior and one or more exterior electrodes are disposed in close relation to the ascending aorta, so that voltage-induced changes can be closely correlated to cardiac events, without significant effects due to non-cardiac physiologic events.

It is known in the medical literature that BIA measurements of cardiac output in general show good correlation for normal patients and hemodynamically stable patients, but much poorer correlation for critically ill patients, and patients in heart failure, as discussed in the above-mentioned Detemeter paper. Applicant has discovered that the reason for this poorer correlation in the latter cases is that the theoretical basis underlying the use of whole body or large-volume thoracic measurements may be incorrect.

Previously known techniques derive the equation for ventricular stroke volume (SV) from the assumption that a time-varying column of blood, in parallel with the other conducting material in the thorax, changes from zero to a volume equal to the stroke volume during the cardiac cycle. The column of blood is assumed to be the length between the electrodes used to obtain the BIA measurements, with effects on the BIA measurements due to respiration accounted for, for example, as discussed in the aforementioned U.S. Pat. No. 4,870,578.

Figure 1A:
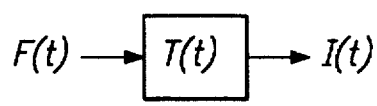
FIGS. 1A and 1B are idealized models of the volumes upon which previously known bioelectrical impedance algorithms are based.

Referring to FIG. 1A, derivation of a typical previously known BIA algorithm is illustrated. Cardiac output is estimated from the bioelectrical impedance measurement I(t), where it is assumed that changes in the bioelectrical impedance coincidental with the heart electrical activity (as represented by an electrocardiograph output) are the result of blood flow F(t). A transfer function T(t) is then based upon empirical formulae derived from measurements taken on healthy, hemodynamically stable subjects. The bioelectrical impedance is then computed as:

$$I(t)=T(t)*F(t)+N(t) \qquad (1)$$

where N(t) is noise.

Applicant has determined, however, that the foregoing assumption regarding the column of blood ignores the branched, multiple and complex paths present in the arterial system. Moreover, the distribution of blood and fluids between different physiologic "compartments" in the idealized thoracic or whole body model and body regions are different in normal and critically ill patients.

Figure 1B:
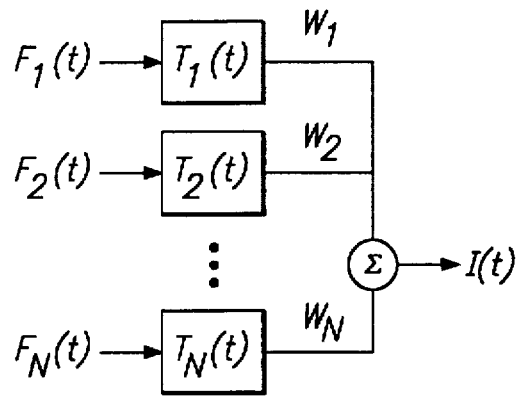

As illustrated in FIG. 1B, the thoracic approach to BIA measurement must account for transfer functions appropriate to each of the multiple blood flow paths through the volume:

$$I(t)=\epsilon F_i(t)*T_i(t)*W_i+N(t) \qquad (2)$$

where $W_i$ are weights corresponding to a priori knowledge of the relative distribution of flow through the various segments of the volume, e.g., the aorta, and arterial segments and other fluid chambers. Moreover, the weights $W_i$ may be different for different patients, may be different for chronically ill as opposed to healthy subjects, and may be variable even within a given patient, e.g., due to changes in heart rate.

Applicant has therefore discovered that equation (1) can be used accurately for any patient provided that the transfer function T(t) is correlated to measured blood flow (e.g., using a flow meter) where the effect of the distribution weights $W_i$ can be essentially eliminated. Accordingly, applicant has concluded that BIA measurements should be taken very close to a blood vessel, so that between the electrodes of the BIA apparatus there are no branching vessels or adjacent vessels. The present invention therefore involves the use of BIA measurements in the vicinity of blood vessels meeting the foregoing requirements.

Figure 2A:
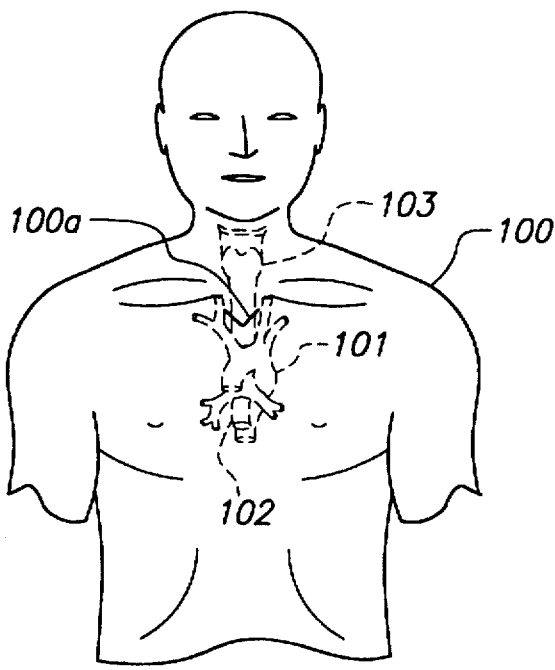
FIGS. 2A and 2B are a vertical frontal view of the upper portion of a human body and a front view of the ascending aorta, the esophagus and the trachea, respectively.
Figure 2B:
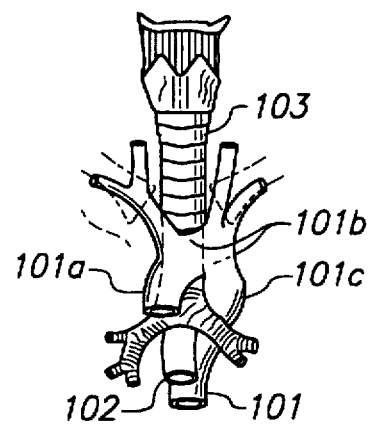

Referring to FIG. 2A, the upper portion of a human body 100 is shown in outline, with the corresponding location of the aorta 101, esophagus 102 and trachea 103 shown in dotted line. These vessels and organs are more clearly depicted in FIG. 2B. With reference to FIGS. 2A and 2B, the outflow tract of the left ventricle of the heart is the ascending aorta 101a. Segment 101b of the artery passes in front of trachea 103 and up towards the base of the neck, then arches 101c towards the lower part of the body.

Applicant has determined that the location of ascending aorta 101a, just beneath the suprasternal notch 100a, provides ready access for an external BIA electrode. In addition, because ascending aorta 101a passes directly in front of trachea 103, it is possible to obtain a BIA measurement across ascending aorta 101a with relatively little intervening tissue. And, because the first branches from the aorta are from aortic arch 101b, the measurement of blood flow from ascending aorta 101a accurately measures the volume of blood ejected from the left ventricle.

Figure 3:
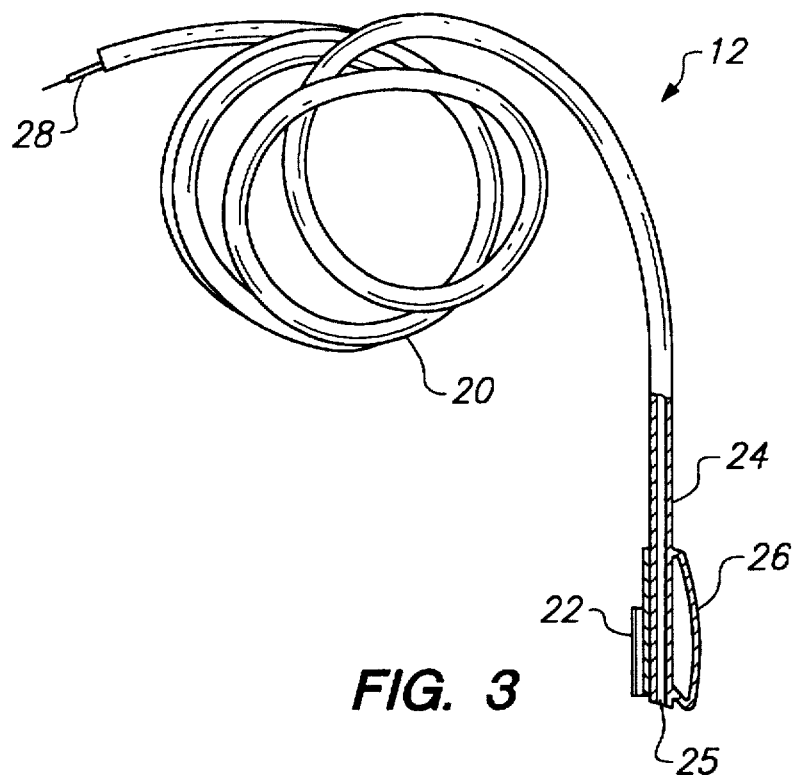
FIG. 3 is a perspective view of a transtracheal electrode constructed in accordance with the present invention, shown with the electrode end in cross section.
Figure 4:
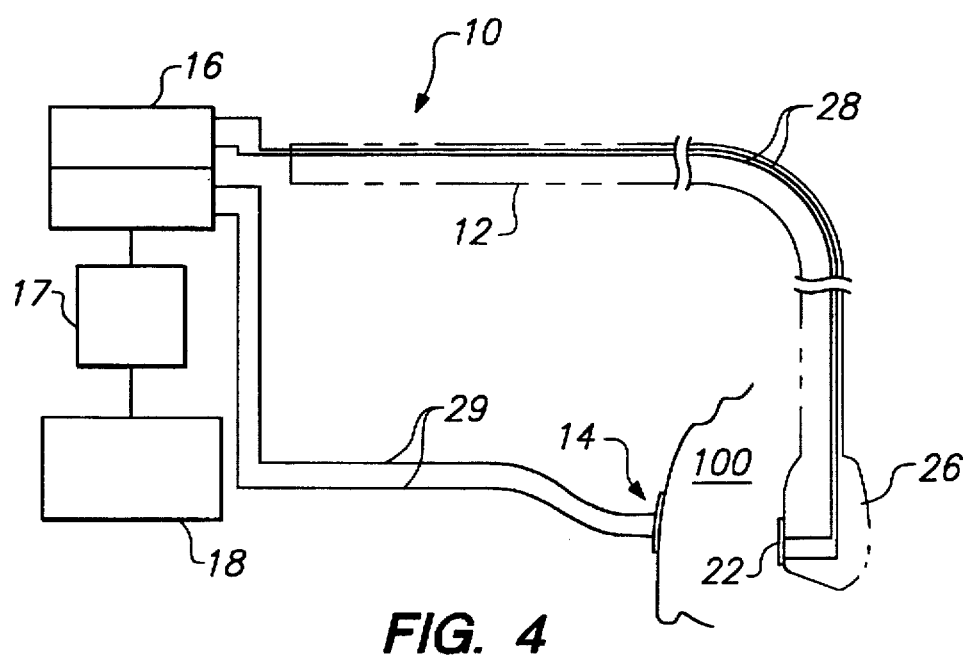
FIG. 4 is a schematic view and block diagram of illustrative apparatus of the present invention.

Referring now to FIGS. 3 and 4, the apparatus of the present invention is described. Apparatus 10 comprises an electrode-bearing endotracheal tube 12, one or more external electrodes 14, impedance recorder 16, digital sampler 17 and computer 18.

As illustrated in FIG. 3, endotracheal tube 12 may comprise a standard endotracheal tube 20 having one or more electrodes 22 disposed on its distal tip 24. Endotracheal tube 12 may also comprise eccentric balloon cuff 26 to ensure good electrical contact between electrode 22 and the interior wall of a patient's trachea. Balloon cuff 26 includes conventional inflation means in fluid communication with balloon cuff through a lumen within endotracheal tube 20. Where balloon cuff 26 is employed, endotracheal tube 20 also includes central lumen 25 to provide ventilation to the patient as well as to permit the administration of oxygen.

Electrode 22 may comprise a 6 mm conductive foil strip, for example, Type M6001, available from the 3M Company, St. Paul, Minn., which is electrically coupled to impedance recorder 16 via electrical leads 28 disposed within, or outside of, endotracheal tube 20. Electrode 22 may be attached directly to the exterior of the endotracheal tube 20, so that the eccentric nature of balloon cuff 26 urges electrode 22 against the tracheal wall. Alternatively, electrode 22 may be disposed on the exterior of balloon cuff 26.

External electrode 14 is placed in the vicinity of the suprasternal notch (see FIG. 1A) for voltage pickup, and is electrically coupled to impedance recorder 16 via leads 29. Electrode 14 may comprise a spot EKG electrode, for example, the AMI 1750-001, manufactured by Medtronic-Andover Medical, Boston, Mass. Additional BIA measurements may be achieved using additional electrodes 14 spaced apart from one another in the vicinity of the suprasternal notch.

Impedance recorder 16 may be a commercially available impedance recorder providing both the sense current (generally less than 1 mA at a frequency of 50–100 kHz) and impedance measuring capability, for example the Minnesota Impedance Cardiograph Model 304A operating at 100 kHz. Signals output from the impedance recorder are digitally sampled by digital sampler 17, for example, at a rate of 250 Hz using a standard 12-bit analog to digital converter, available from ComputerBoards, Inc., Mansfield, Mass. The sampled output of digital sampler 17 is then provided to computer 18, for example, an IBM-compatible personal computer having an Intel 386 or higher microprocessor, for storage and processing, as described hereinbelow.

Figure 5:
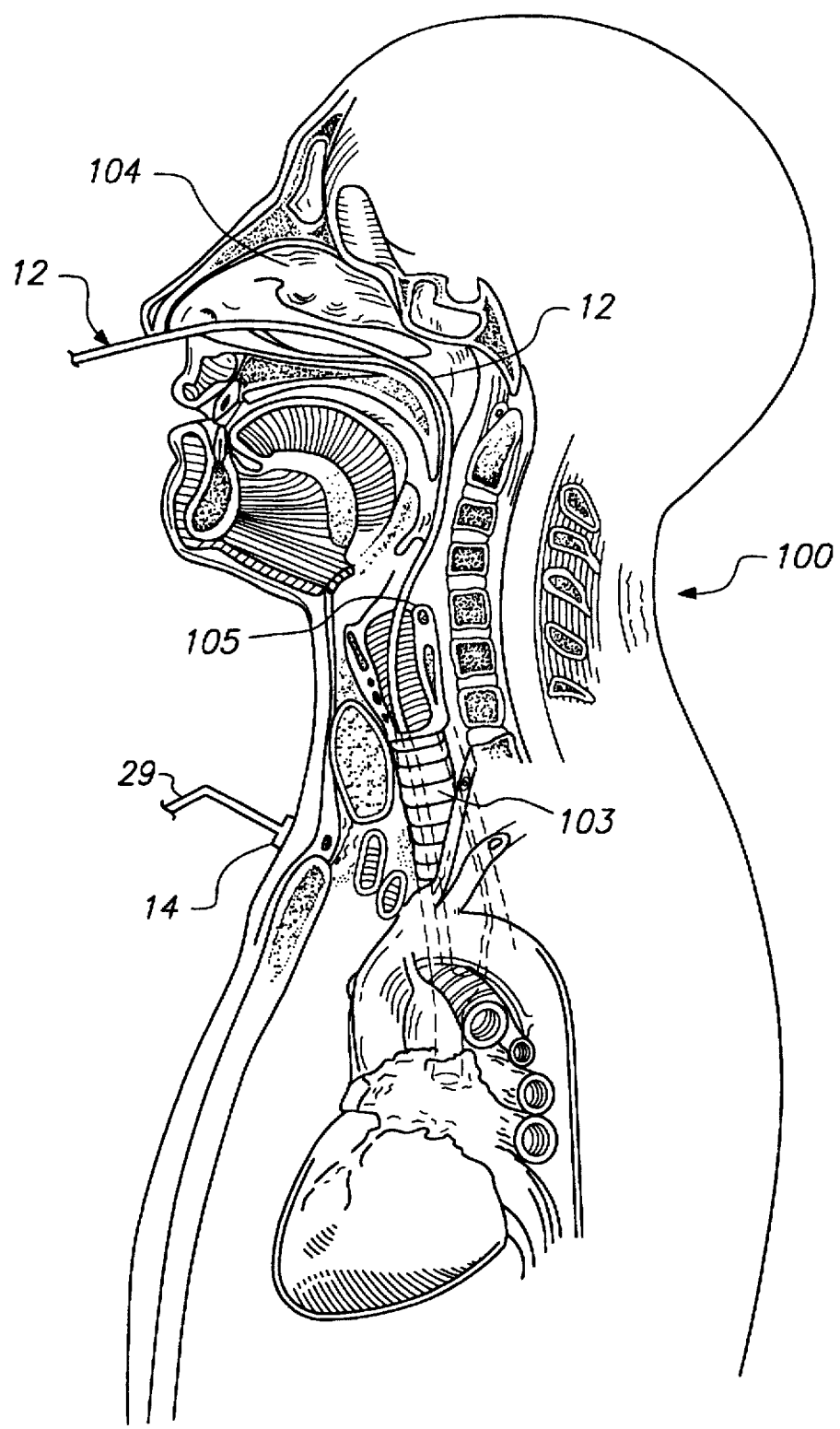
FIG. 5 is vertical cross-sectional view of the upper portion of a human body showing the arrangement of the electrodes of the apparatus of the present invention.

Referring now to FIG. 5, arrangement of the electrodes 22 and 14 are described. Endotracheal tube 20 is inserted into patient 100 through nasal cavity 104, past epiglottis 105 and into trachea 103 in accordance with standard medical practice. If the apparatus of the present invention is to be used for only a relatively short period of time, e.g., while a patient is anesthetized during surgery, endotracheal tube 20 may be inserted into the trachea via the mouth. Alternatively, access to trachea 103 may be had through a surgical opening at the suprasternal notch 100a by conventional tracheotomy.

One or more electrodes 14 are placed on the exterior of the patient near the suprasternal notch, so that the primary path for the excitation current is through the ascending aorta to electrode 22, with relatively little intervening tissue in the current path as compared to previously known BIA measurement techniques.

Figure 6:
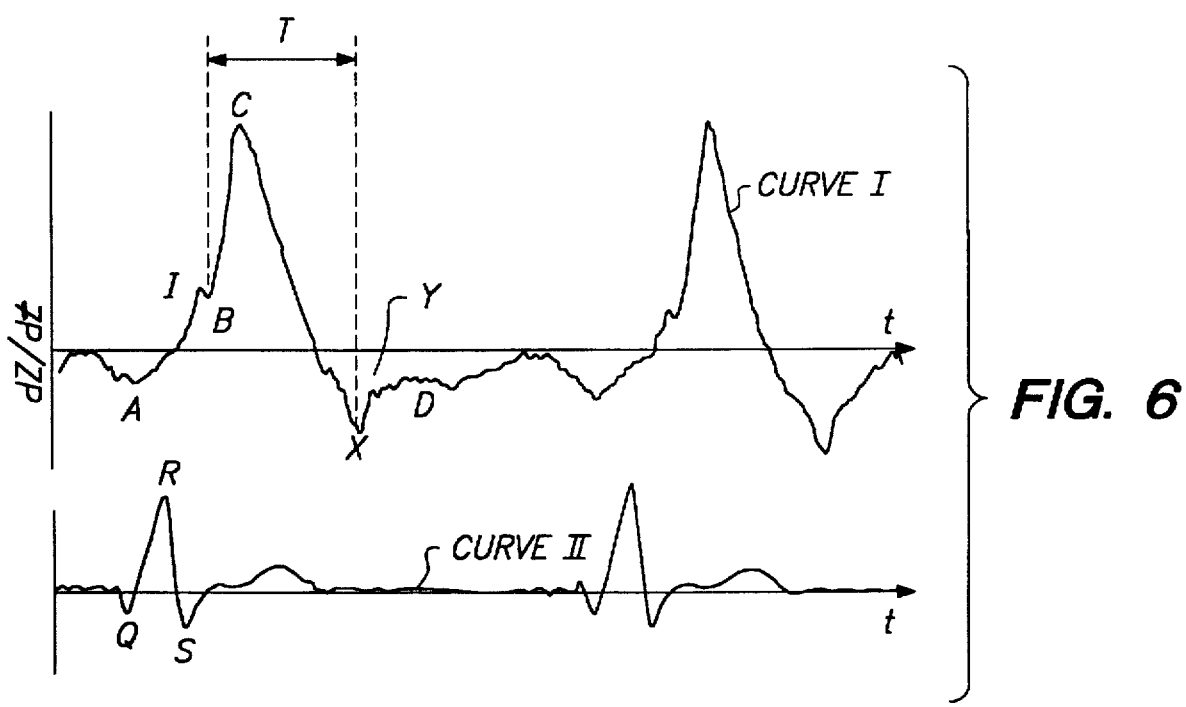
FIG. 6 is a graph showing the relationship between cardiac events and the first derivative of the measured bioelectrical impedance.

Referring now to FIG. 6, the first derivative of the measured impedance (dZ/dt) (curve I) is compared to a typical electrocardiograph waveform (curve II) for a normal patient, where the components of the waveform describing events within the cardiac cycle are labelled. Curve I includes an A-wave component, due to atrial activity at the beginning of the cardiac cycle, represented by a downward deflection in the curve. The I-wave component represents an upward deflection in curve I occurring during isometric contraction. The B-wave component corresponds to the start of blood flow out of the ventricles, while the C-wave component of curve I represents the major upward deflection during the cardiac cycle. The amplitude of this deflection measured from the zero point is used in the calculation of the ventricular stroke volume SV. The X and Y points of curve I reflect closure of the aorta and pulmonary valves, respectively. Point O corresponds to rapid filling of the ventricles.

SV is calculated according to equation 3:

$$SV = rho(L/Z_0)^2 (dZ/dt_p) T \quad (3)$$

where:

SV=ventricular stroke volume, ml rho=resistivity of blood (in normal patients, about 150 ohm-cm/s, and can be corrected for each patient as a function of hematocrit)

L=distance between the electrodes, cm $Z_0$=mean impedance between the measurement electrodes, ohms $dZ/dt_p$=peak value of the upward deflection in the first derivative of the impedance waveform (amplitude of C-wave)

T=ventricular ejection time (computed as the period between the occurrence of the B-wave component and point X in curve I).

The digitized first derivative of the measured impedance is analyzed to extract the B-wave and C-wave components and the X deflection point. The amplitude of the B-C-X portion of the curve I waveform, and the time between these segments are then employed to compute stroke volume using equation 3. The distance between the electrodes L may be computed based on external body measurements.

In a preferred embodiment of the invention, SV is continuously computed for each data segment that is of good signal quality, i.e., where the amplitude of the derivative of the impedance signal is above a certain quality metric. The SV may be continuously updated on a display (not shown) associated with computer 18, and may consist of a running average of the current and a user-selectable number of preceding cardiac cycles. Cardiac output may then be computed as the product of the instantaneous average SV and the heart rate, and also displayed numerically.

Applicant expects that the transtrachealsuprasternal BIA measurement technique in accordance with the present invention will not be significantly affected by motion artifacts or electrode placement. In addition, because leads 28 and 29 can be relatively short, it is expected that the apparatus of the present invention will be less susceptible to electrical interference.

In addition, as indicated hereinabove, alternative embodiments of the apparatus of the present invention may include multiple electrodes 22 on the endotracheal tube 24 and multiple external electrodes 14 for measuring the bioelectrical impedance. Alternative embodiments may also include additional sensors to enable additional quantitative analysis. For example, diodes suitable for employing blood oximetry techniques based on near infrared light absorption may also disposed on the internal and external sensors to measure blood oxygen saturation levels.

Figure 7A:
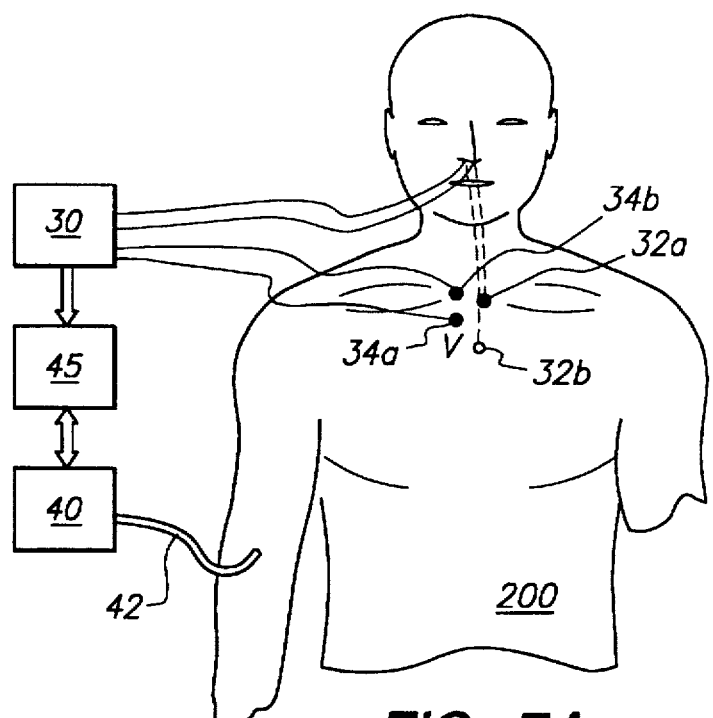
FIGS. 7A and 7B are schematic diagrams showing systems for administering fluids to a patient and for controlling heart rate for patients having pacemakers, respectively, constructed in accordance with the principles of the present invention.

Referring to FIG. 7A, another embodiment of the present invention is described as controller for fluids administration. In FIG. 7A, cardiac output is measured by apparatus 30 having two transtracheal electrodes 32a and 32b and two external electrodes 34a and 34b disposed on patient 200. Apparatus 30 functions as described hereinabove with respect to the apparatus of FIG. 4, and is used to monitor hemodynamic status and as a metric to control the administration of fluids intravenously via lumen 42 coupled to fluid supply system 40. Computer 45, which may be an IBM-compatible PC (and the same computer that computes cardiac output from the measured values of bioelectrical impedance), controls fluid supply system 40.

Operation of the apparatus of FIG. 7A is as follows. After a one unit loss of blood, for example, it is known that cardiac output changes but that heart rate and blood pressure do not. Thus, decreased cardiac output can be used to monitor the amount of fluids to be given to a patient. The apparatus of FIG. 7A provides a closed-loop system wherein the amount of fluid injected into the patient is controlled by the cardiac output computed as described hereinabove.

In FIG. 7A, a baseline cardiac output measurement is obtained and then a bolus of 50 cc of fluid is given while cardiac output is measured continuously. As long as the cardiac output increases, additional boluses of fluid are given periodically, e.g., every 15 minutes. This process may be repeated several times a day for a critically ill patient.

Figure 7B:
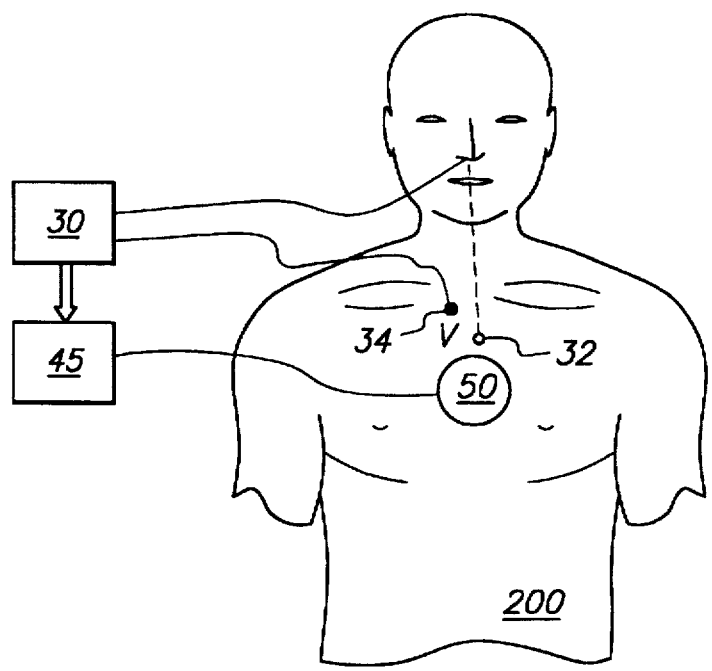

Referring to FIG. 7B, an alternative embodiment of the present invention is described in which apparatus 30 and computer 45 of FIG. 7A are used to control a pacemaker. It is desirable to maximize cardiac output for the lowest possible heart rate, since the lower the heart rate, the lower the myocardial oxygen consumption. In the arrangement of FIG. 7B, computer 45 controls the setting of pacemaker 50 as described hereinafter.

A baseline cardiac output measurement is first obtained and then the heart rate is reduced by a predetermined amount, e.g., two beats/min, while the cardiac output is continuously monitored by apparatus 30. As long as the cardiac output increases or remains unchanged, the heart rate is periodically further lowered by the predetermined amount, for example, by 2 beats/min every 15 minutes. The process of reducing heart rate while monitoring cardiac output is continued until either a minimum desired heart rate is obtained or the cardiac output measured by apparatus 30 begins to decrease. If the cardiac output is determined to have decreased, the heart rate is returned to the preceding higher rate.

While preferred illustrative embodiments of the present invention are described above, it will be obvious to one skilled in the art that various changes and modifications may be made therein without departing from the invention and it is intended in the appended claims to cover all such changes and modifications which fall within the true spirit and scope of the invention.

What is claimed is:

1. Apparatus for determining the cardiac output of a patient, the apparatus comprising:

a first electrode adapted to be disposed within the trachea of the patient;

a second electrode adapted to be disposed on the exterior of the thorax of the patient;

a bioelectrical impedance recorder providing an output, the bioelectrical impedance recorder coupled to the first and second electrodes to pass a current therebetween; and means for processing the output of the bioelectrical impedance recorder to compute a metric corresponding to the patient's cardiac output.

2. Apparatus as defined in claim 1 further comprising an endotracheal tube having a proximal end and a distal end, the first electrode being disposed upon the distal end.

3. The apparatus as defined in claim 2 further comprising a third electrode coupled to the bioelectrical impedance recorder and disposed upon the distal end.

4. Apparatus as defined in claim 1 wherein the second electrode is adapted to be disposed on the skin of the patient in the vicinity of the suprasternal notch.

5. The apparatus as defined in claim 4 further comprising a fourth electrode coupled to the bioelectrical impedance recorder and adapted to be disposed on the skin of the thorax in the vicinity of the suprasternal notch.

6. The apparatus as defined in claim 2 wherein the endotracheal tube further comprises an inflatable cuff.

7. The apparatus as defined in claim 6 wherein the first electrode is disposed upon the inflatable cuff.

8. The apparatus as defined in claim 6 wherein the endotracheal tube further comprises a lumen for inflating the inflatable cuff, and the inflatable cuff permits ventilation of the patient when inflated.

9. The apparatus as defined in claim 1 further comprising a fluid administration system for injecting a bolus of fluid into the vascular system of the patient, the fluid administration system coupled to the means for processing and responsive to the metric corresponding to the cardiac output.

10. The apparatus as defined in claim 1 further comprising a pacemaker controlling the heart rate of the patient, the pacemaker coupled to the means for processing and responsive to the metric corresponding to the cardiac output.

11. The apparatus as defined in claim 1 wherein the means for processing comprises a suitably programmed IBM-compatible computer.

12. The apparatus as defined in claim 11 wherein the means for processing further comprises circuitry for digitizing the output of the bioelectrical impedance recorder.

13. A method of measuring the cardiac output of a patient comprising steps of positioning a first electrode within the trachea of the patient in the vicinity of the ascending aorta;

positioning a second electrode on the exterior of the thorax of the patient in the vicinity of the suprasternal notch;

applying a voltage between the first and second electrodes so that a current flows through the tissues of the patient between the first and second electrodes; and detecting a voltage developed across the first and second electrodes caused by the current flowing in the tissues of the patient, the voltage varying in accordance with changes in the electrical bioimpedance of the tissues.

14. The method as defined in claim 13 wherein the first electrode is disposed on an endotracheal tube and the step of positioning the first electrode further comprises a step of inserting the endotracheal tube in the trachea of the patient through a nasal cavity of the patient.

15. The method as defined in claim 13 wherein the first electrode is disposed on an endotracheal tube and the step of positioning the first electrode further comprises a step of inserting the endotracheal tube in the trachea of the patient through the mouth of the patient.

16. The method as defined in claim 13 wherein the first electrode is disposed on an endotracheal tube and the step of positioning the first electrode further comprises a step of inserting the endotracheal tube in the trachea of the patient through a tracheotomy port.

17. The method as defined in claim 13 wherein the first electrode is disposed on an endotracheal tube having an inflatable cuff and the step of positioning the first electrode further comprises a step of inflating the inflatable cuff.

18. The method as defined in claim 13 wherein the steps of applying the voltage and detecting a voltage developed across the first and second electrodes are performed continuously.

19. The method as defined in claim 13 further comprising steps of:

providing a fluid administration system for injecting a bolus of fluid intravenously into the patient's vascular system;

periodically actuating the fluid administration system on responsive to the detected voltage developed across the first and second electrodes.

20. The method as defined in claim 19 wherein the step of periodically actuating the fluid administration system is performed every 15 minutes only while the cardiac output is measured to be increasing.

21. The method as defined in claim 13 further comprising steps of:

providing a pacemaker electrically coupled to the heart of the patient to control heart rate; and adjusting the heart rate responsive to voltage developed across the first and second electrodes to optimize cardiac output.

22. The method as defined in claim 21 wherein the step of adjusting the heart rate comprises a step of lowering the heart rate to obtain either a predetermined minimum heart rate or until the cardiac output is measured to be decreasing.

23. The method as defined in claim 22 wherein the step of lowering the heart rate comprises adjusting the heart rate downward by two beats per minute every 15 minutes.

* * * * *